(12) United States Patent
Vestal

(10) Patent No.: US 7,705,325 B2
(45) Date of Patent: Apr. 27, 2010

(54) STERILIZATION DEVICE FOR A STETHOSCOPE AND ASSOCIATED APPARATUS

(76) Inventor: Mark Vestal, 438 Robeson St., Fayetteville, NC (US) 28301

( * ) Notice: Subject to any disclaimer, the term of this patent is extended or adjusted under 35 U.S.C. 154(b) by 108 days.

(21) Appl. No.: 12/034,927

(22) Filed: Feb. 21, 2008

(65) Prior Publication Data

US 2009/0212234 A1    Aug. 27, 2009

(51) Int. Cl.
*A61L 2/00* (2006.01)
*A61L 2/18* (2006.01)

(52) U.S. Cl. ............... 250/455.11; 250/453.11; 250/454.11; 250/504 R

(58) Field of Classification Search ........... 250/453.11, 250/454.11, 455.11, 504 R
See application file for complete search history.

(56) References Cited

U.S. PATENT DOCUMENTS

| | | | |
|---|---|---|---|
| 4,461,368 A | 7/1984 | Plourde | |
| 5,892,233 A | 4/1999 | Clement | |
| 6,579,495 B1 | 6/2003 | Maiden | |
| 7,360,625 B2 * | 4/2008 | Stickley | 181/131 |
| 7,406,973 B1 * | 8/2008 | Perlman et al. | 134/166 R |
| 7,503,335 B2 * | 3/2009 | Perlman et al. | 134/166 R |
| 2002/0074559 A1 * | 6/2002 | Dowling et al. | 257/99 |
| 2002/0146343 A1 | 10/2002 | Jenkins et al. | |
| 2002/0162972 A1 | 11/2002 | Pleet | |
| 2005/0236579 A1 | 10/2005 | Jenkins et al. | |
| 2005/0254992 A1 | 11/2005 | Jenkins et al. | |
| 2006/0147339 A1 | 7/2006 | Hunter et al. | |
| 2007/0080017 A1 | 4/2007 | Stickley | |
| 2008/0265179 A1 * | 10/2008 | Havens et al. | 250/492.1 |

FOREIGN PATENT DOCUMENTS

WO    WO 2005/110001 A1    11/2005

* cited by examiner

*Primary Examiner*—David A Vanore
(74) *Attorney, Agent, or Firm*—Alston & Bird LLP

(57) ABSTRACT

A sterilization device for a stethoscope is provided, comprising a cover member and an ultraviolet light source. The stethoscope includes a chestpiece member having a face portion adapted to contact a patient. The cover member is adapted to operably engage the chestpiece member such that the cover member is movable with respect to the face portion and normally biased to cover the face portion. The ultraviolet light source is operably engaged with the cover member and configured to emit ultraviolet radiation for interacting with the face portion only when the cover member is covering the face portion. The ultraviolet light source thereby provides anti-microbial sterilization of at least the face portion of the chestpiece member. An associated apparatus is also provided.

23 Claims, 3 Drawing Sheets

STERILIZATION DEVICE FOR A STETHOSCOPE AND ASSOCIATED APPARATUS

BACKGROUND OF THE INVENTION

1. Field of the Invention

The present disclosure relates to stethoscopes and, more particularly, to a sterilization device for a stethoscope and associated apparatus.

2. Description of Related Art

Since a stethoscope includes a "chestpiece" that typically contacts the patient being examined, it may be desirable to be able to sterilize at least the contact surface of the chestpiece prior to using the stethoscope on a subsequent patient. However, accomplishing such sterilization may not often be practical, in terms of the required time or the particular procedures that must be followed. Also, the practitioner may not necessarily have the training or discipline to routinely perform such sterilization between patients, or may not necessarily remember whether sterilization has been performed prior to using the stethoscope on the next patient.

Thus, there exists a need for an apparatus configured to promote and facilitate convenient and efficient sterilization of at least the contact surface of a "chestpiece" member of a stethoscope between uses.

BRIEF SUMMARY OF THE INVENTION

The above and other needs are met by the present disclosure which, in one embodiment, provides a sterilization device configured to engage a chestpiece member of a stethoscope, the chestpiece member having a face portion adapted to contact a patient. Such a sterilization device comprises a cover member adapted to operably engage the chestpiece member such that the cover member is movable with respect to the face portion and normally biased to cover the face portion. An ultraviolet light source is operably engaged with the cover member and configured to emit ultraviolet radiation for interacting with the face portion only when the cover member is covering the face portion. The ultraviolet light source thereby provides anti-microbial sterilization of at least the face portion of the chestpiece member.

Another advantageous aspect of the present invention comprises a stethoscope including a chestpiece member having a face portion adapted to contact a patient and to transmit sound therefrom to a binaural member. An ultraviolet light source is operably engaged with the chestpiece member. The ultraviolet light source is configured to emit ultraviolet radiation for interacting with the face portion to provide anti-microbial sterilization of at least the face portion of the chestpiece member.

Thus, the sterilization device and stethoscope, as disclosed in conjunction with various embodiments of the present disclosure, provide many advantages that may include, but are not limited to, conveniently and efficiently providing anti-microbial sterilization for the stethoscope between uses.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

Figure 2A:
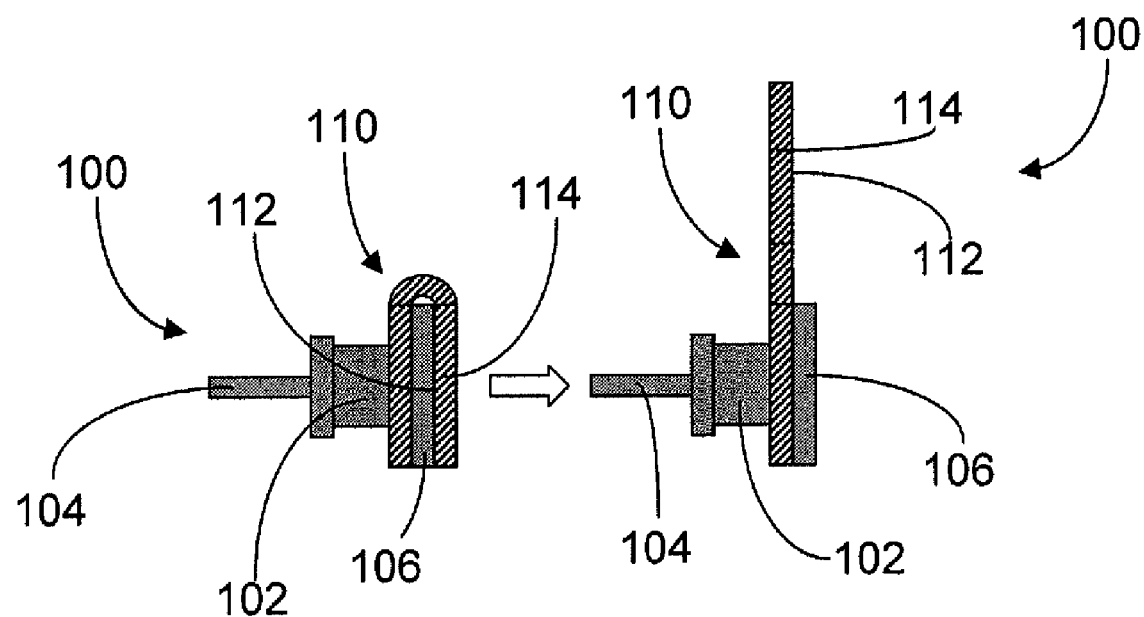
FIG. 2A illustrates a side elevation schematic of a sterilization device moving in a flip-over manner from a covered position to an uncovered position with respect to a face portion of a stethoscope in accordance with one aspect of the present disclosure.
Figure 2B:
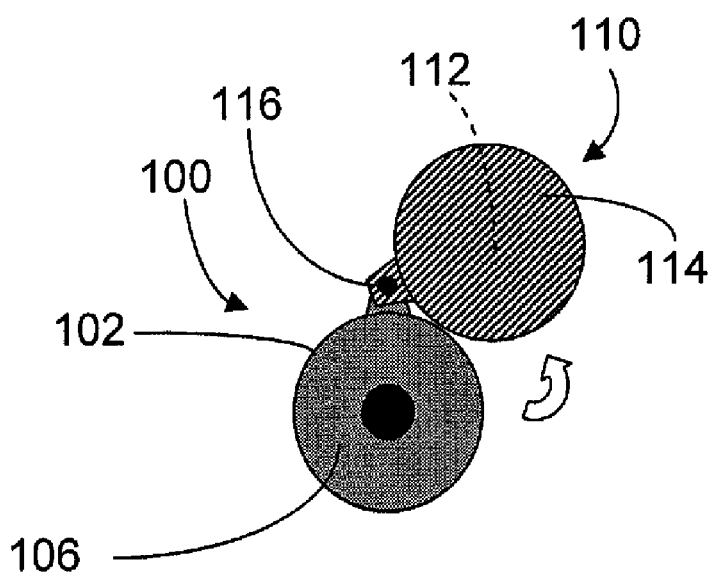
Figure 3A:
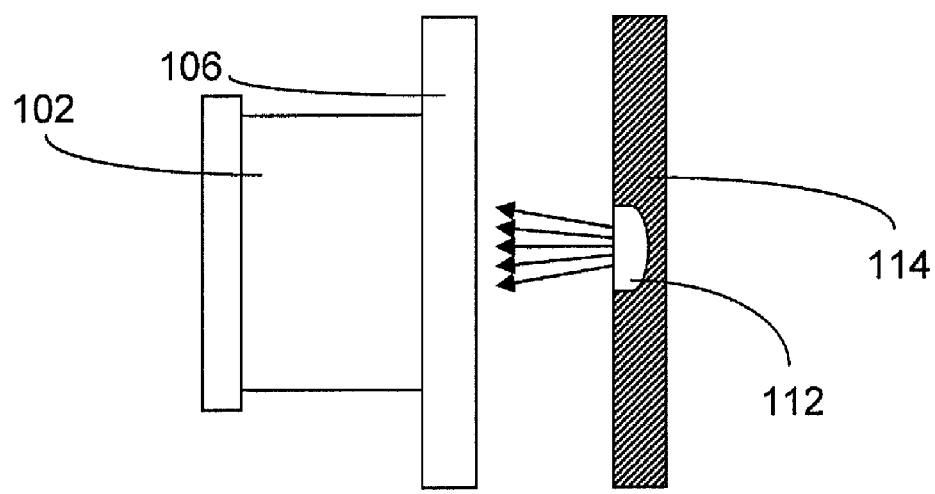
Figure 3B:
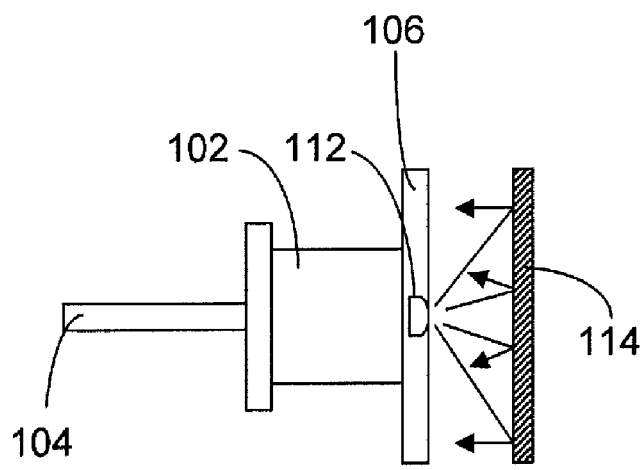
Figure 3C:
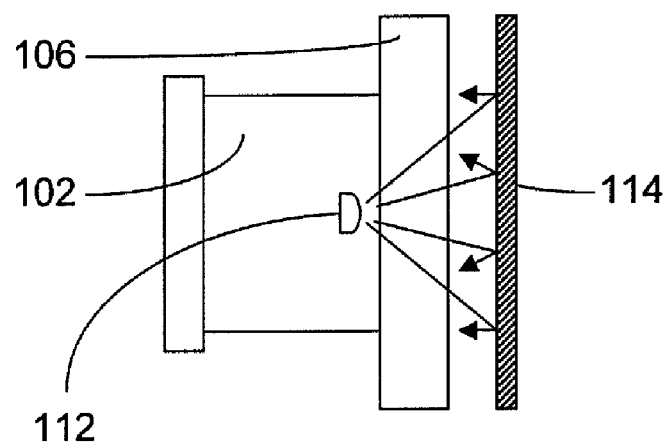

FIG. 2B illustrates a front elevation schematic of a sterilization device having a cover member movable in a pivotable manner and being in an uncovered position with respect to a face portion of a stethoscope in accordance with one aspect of the present disclosure; and FIGS. 3A-3C illustrate various cross-sectional side views of a sterilization device emitting ultraviolet radiation from an ultraviolet light source such that the ultraviolet radiation interacts with a chestpiece member of a stethoscope in accordance with some embodiments of the present disclosure.

DETAILED DESCRIPTION OF THE INVENTION

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Figure 1:
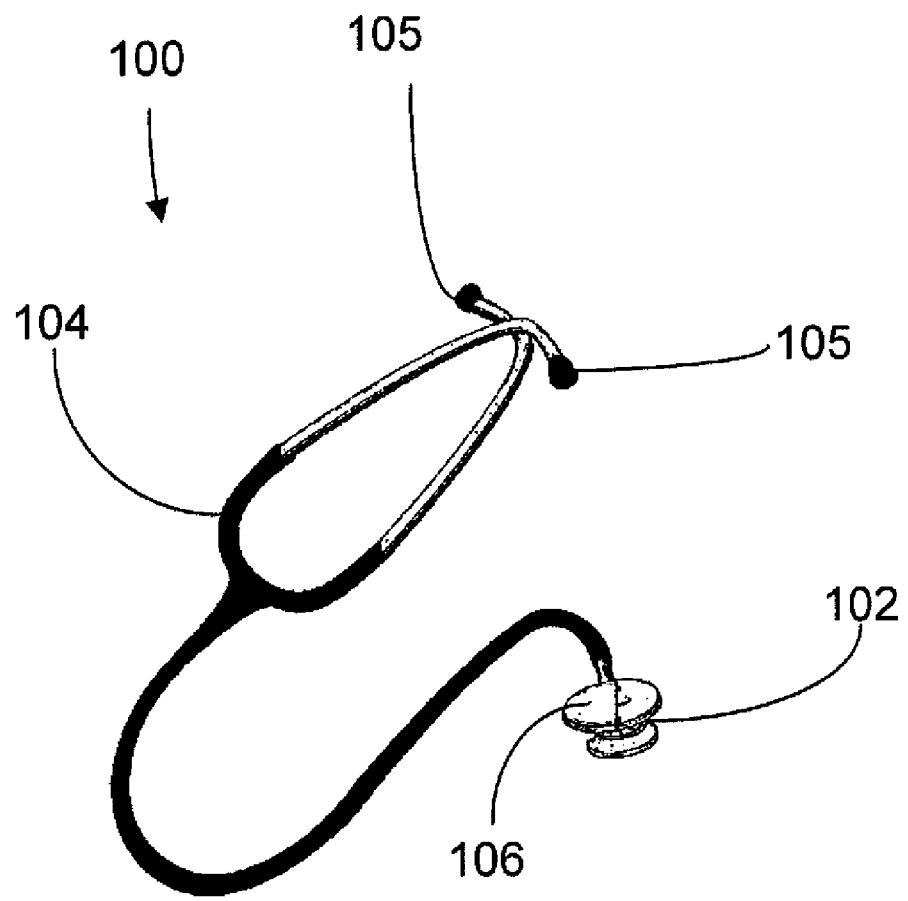
FIG. 1 illustrates a perspective view of a stethoscope device according to one embodiment of the present disclosure.

As shown in FIG. 1, a stethoscope, generally designated 100, may generally comprise a chestpiece member 102 adapted to operably engage a binaural member 104. Chestpiece member 102 may include a face portion 106 that is adapted to contact a patient and to transmit sound therefrom to binaural member 104. Binaural member 104 may include aural elements 105 adapted to be positioned within or otherwise in engagement with the practitioner's ears for auscultation, for example, of heart sounds and breathing of the patient. Face portion 106 of the chestpiece member 102 of an acoustic stethoscope may include a diaphragm (i.e., a plastic disc) that is vibrated by body sounds when the diaphragm contacts a patient. Accordingly, acoustic pressure waves are created that travel to the practitioner's ears via the binaural member 104. Face portion 106 may be, in some instances, substantially flat or, in other instances, generally bell or cone shaped. Although the present disclosure is described herein with respect to acoustic stethoscopes, the present disclosure may also apply to other stethoscopes, such as electronic stethoscopes, without departing from the scope of the disclosure, and is in no way limited to acoustic stethoscopes.

With reference to FIGS. 2A and 2B, a sterilization device, generally designated 110, may be provided for use with stethoscope 100 in accordance with one aspect of the present disclosure. Sterilization device 110 may be adapted to sterilize face portion 106 between uses thereof so as to, for example, limit the spread of germs and bacteria on chestpiece member 102 between subsequent patients. Sterilization device 110 may be configured to operably engage chestpiece member 102 in any suitable manner such as, for example, being clipped, fastened, fixed, or attached to chestpiece member 102 for permanent (i.e., integral or built-in) or temporary (i.e., as an accessory) engagement. One skilled in the art will appreciate that, even though the sterilization device 110 is described in exemplary instances as an accessory to a stethoscope 100, the structure and components of some aspects of such a sterilization device 110 may be "built in" or otherwise integrated with a stethoscope 100 itself, as otherwise discussed herein, such that the sterilizing device is integral with the stethoscope apparatus, as shown for example in FIGS. 3B and 3C. To provide appropriate sterilization of at least the face portion 106 of the chestpiece member 102, sterilization device 110 may comprise an ultraviolet light source 112 configured to emit ultraviolet radiation for interacting with and sterilizing face portion 106 of chestpiece member 102. As an example, ultraviolet light source 112 may comprise at least one light emitting diode (LED) capable of emitting ultraviolet light, which one skilled in the art will recognize as being effective in the elimination of harmful bacterial and other cellular organisms (i.e., for anti-microbial sterilization) that may cause sickness and disease in humans. By having sterilization device 110 operably engaged with chestpiece member 102, ultraviolet light source 112 may be configured to emit ultraviolet radiation for interaction with face portion 106 of chestpiece member 102 for sterilization thereof in a convenient and reliable manner for the practitioner.

Further, it may be desirable to contain the emission of the ultraviolet radiation by ultraviolet light source 112 such that the radiation is directed to interact with face portion 106 without leakage that may reach the patient or practitioner through stray emissions. Thus, sterilization device 110 may comprise a cover member 114 adapted to operably engage chestpiece member 102 such that cover member 114 is movable with respect to face portion 106 and normally biased to cover face portion 106. That is, cover member 114 may be moveable between a closed position in which it covers and opposes face portion 106, and an open position in which it does not cover face portion 106 (i.e., allowing the chestpiece member 102 of the stethoscope 100 to be used in a normal manner), while remaining operably engaged with chestpiece member 102. Further, ultraviolet light source 112 may be configured to operably engage cover member 114, such that ultraviolet light source 112 is correspondingly movable with cover member 114 between a closed position opposing face portion 106 and an open position not covering face portion 106 (see, e.g., FIG. 3A). As such, ultraviolet light source 112 may be incorporated into cover member 114 in any suitable manner. For example, ultraviolet light source 112 may be fixed, fastened, attached, or integral to cover member 114 so as to correspondingly move therewith.

To prevent stray emissions of the ultraviolet radiation, cover member 114 is configured to cover and oppose face portion 106 when ultraviolet light source 112 is actuated to emit the ultraviolet light. In furtherance of limiting such emissions, the cover member 114 may be further configured to cooperate with the face portion 106 so as to form an emission-limiting seal therewith when the cover member 114 is in the closed position with respect to the face portion 106. Also, cover member 114 may be moved to the open position in which face portion 106 is not covered thereby so as to permit the practitioner to place chestpiece member 102 against the patient and use stethoscope 100 as intended, wherein ultraviolet light source 112 is not actuated. That is, the sterilization device 110 may be desirably configured such that the ultraviolet light source 112 is only actuated when the face portion 106 is covered by the cover member 114 and, in one instance, only when the emission-limiting seal is formed between the face portion 106 and the cover member 114. Some embodiments may include an actuation device (not shown) operably engaged between the cover member 114 and the chestpiece member 102 for actuating the ultraviolet light source 112 only when the face portion 106 is covered by the cover member 114. In some aspects, cover member 114 may also include a reflective material disposed on an interior surface thereof (or at least have an interior surface configured to be reflective to the ultraviolet radiation) such that the reflective material opposes face portion 106 when cover member 114 is positioned to cover face 106. As such, ultraviolet light emitted from ultraviolet light source 112 may be reflected and directed toward face portion 106 by the reflective material to be more evenly distributed over and to more effectively and efficiently sterilize face portion 106.

In some embodiments, as shown in FIG. 2A, sterilization device 110 may be pivotably attached (i.e., "hinged") to chestpiece member 102 such that the cover member 114 rotates substantially perpendicularly to the face portion 106 in a "flip-over" configuration with respect thereto for selectively covering and uncovering the face portion 106. That is, sterilization device 110 may be attached to chestpiece member 102 such that a portion thereof (i.e., an attachment element) remains immovable or with limited movability with respect to chestpiece member 102 while the cover member 114 rotatably engaged therewith is capable of flipping closed over face portion 106. For instance, cover member 114 may be normally biased to the "closed" position in covering relation with the face portion 106 by a biasing member, such as an appropriate spring. In such instances, the cover member 114 will move to a closed portion covering the face portion 106 of chestpiece member 102 when the stethoscope 100 is not in use. In other aspects, when covering face portion 106, at least a portion of cover member 114 (i.e., about the interior surface) may contact face portion 106 so as to form the emission-limiting seal therewith. In other instances, as will be appreciate by one skilled in the art, the emission-limiting seal may be formed by an appropriate sealing member (not shown) operably engaged with one of the chestpiece member 102 and the cover member 114. As illustrated in FIG. 2A, cover member 114 may be configured to flip-over face portion 106 in a downward manner, but may be oriented in many different manners as necessary or desirable, for example, for ergonomic reasons or to accommodate a right-handed or left-handed practitioner.

According to other embodiments, as illustrated in FIG. 2B, sterilization device 110 may be pivotably attached to the chestpiece member 102 (i.e., by an attachment element) such that the cover member 114 rotates substantially parallel to the face portion 106 so as to "swivel" laterally with respect thereto for selectively covering and uncovering the face portion 106. For instance, the sterilization device 110 may have the cover member 114 attached at a pivot point 116 such that cover member 114 can pivot laterally thereabout to cover or uncover face portion 106. Cover member 114 may be pivotably attached directly to chestpiece member 102, or in other embodiments pivotably attached with respect to the portion of sterilization device 110 that is operably engaged with chestpiece member 102. Furthermore, when covering face portion 106, at least a portion of cover member 114 may contact or abut face portion 106 to at least partially form the emission-limiting seal therewith. In another aspect, a biasing member (not shown) may be operably engaged between the cover member 114 and the chestpiece member 102, with the biasing member being configured to normally bias the cover member 114 to cover the face portion 106 (i.e., to laterally swivel the cover member 114 back to the "closed" position over the face portion 106, when the stethoscope 100 is not in use).

In other embodiments, sterilization device 110 may be operably engaged with chestpiece member 102 in an "iris" configuration. In such embodiments (not shown), cover member 114 may be configured as an iris actuatable between an open position and a closed position, wherein cover member 114 covers face portion 106 when the iris is closed Accordingly, the ultraviolet radiation source 112 is actuated only when the iris is closed. In light of such embodiments, one skilled in the art will appreciate that the cover member 114/ sterilization device 110 may take many different forms consistent with the scope of the disclosure, and that the embodiments disclosed herein are not intended to be limiting in that respect.

Accordingly, as illustrated in FIGS. 2A and 2B, cover member 114 may be movable from a closed position directly covering and opposing face portion 106 to an open position wherein face portion 106 is not covered, thereby allowing a practitioner to place face portion 106 against a patient for auscultation. Similarly, cover member 114 may be movable from the open (uncovered) to position with respect to face portion 106, to the closed position directly covering and opposing face portion 106, thereby positioning ultraviolet light source 112 in proximity to face portion 106 such that, when actuated, ultraviolet radiation is directed toward face portion 106. Preferably, cover member 114 is normally biased to cover face portion 106 of chestpiece member 102, although one skilled in the art will recognize that the cover member may not be biased at all (i.e., manually opened and closed) or normally biased so as not to cover face portion 106 (i.e., must be manually closed to actuate the sterilization process). As illustrated in FIG. 3A, when cover member 114 is positioned to cover face portion 106, ultraviolet light source 112 may be actuated to provide anti-microbial sterilization of face portion 106 by emitting ultraviolet light for interacting with face portion 106. Further, cover member 114 may include a sealing mechanism configured to form a sealing engagement with face portion 106 so as to prevent stray emission of ultraviolet radiation.

In some aspects, ultraviolet light source 112 may comprise an LED or other radiation source configured to emit ultraviolet light, as will be appreciated by those skilled in the art. In some instances, the LED may be battery-powered. In such embodiments, sterilization device 110 may be adapted to provide a re-charging capability for the battery. Further, ultraviolet light source 112 may be actuated by a contact switch, a limit switch, or any other suitable actuation device, such as a timer. In some embodiments, ultraviolet light source 112 may be actuated by photo detectors operating as a switch to activate the sterilization process when the face portion 106 is covered by the cover member 114. Preferably, the actuation device is configured to actuate ultraviolet light source 112 only when cover member 114 is closed over face portion 106 of chestpiece member 102, thereby preventing undesirable emission of ultraviolet radiation. Additionally, the actuation device may be configured to maintain ultraviolet light source 112 "on" (i.e., emitting the ultraviolet radiation) for a sufficient period of time to effectively sterilize face portion 106. Further, a "lock-out" device may also be provided that may, in some instances, prevent the cover member 114 from being moved to an open position before the sterilization time has elapsed, for example, provide an indicia that appropriate sterilization of the face portion 106 has not been accomplished.

According to other embodiments of the present disclosure, ultraviolet light source 112 may be configured to be operably engaged with chestpiece member 102 in addition to, or in the alternative from, operably engaging cover member 114. In some embodiments, as generally shown in FIGS. 3B and 3C, ultraviolet light source 112 may be generally incorporated, built-in, or disposed on or within chestpiece member 102 such that ultraviolet radiation is emitted from or from within chestpiece member 102 to interact with face portion 106 (in such instances, the sterilization device may be an integral part of a stethoscope apparatus, instead of an accessory for a stethoscope apparatus). For example, an LED ultraviolet light source 112 capable of emitting ultraviolet light may be incorporated into chestpiece member 102 in any suitable manner.

In one instance, the face portion 106 of the chestpiece member 102 may comprise an ultraviolet radiation-transparent material, and the ultraviolet light source 112 may be disposed within the chestpiece member 102 (see, e.g., FIG. 3C) such that ultraviolet radiation emitted therefrom is directed through the ultraviolet radiation-transparent material to provide anti-microbial sterilization of at least the face portion 106 of the chestpiece member 102 (albeit from within the chestpiece member 102). In such embodiments, face portion 106 may be formed, for instance, from any suitable ultraviolet radiation-transparent material (i.e., plastic, glass, etc.) so as to permit the emitted ultraviolet light to be transmitted therethrough to interact with and sterilize face portion 106. The portion of chestpiece member 102 not comprising face portion 106 may be of a material that absorbs, blocks, or is otherwise opaque with respect to ultraviolet light, thereby preventing escape of ultraviolet radiation from the chestpiece member 102 other than through face portion 106. In other embodiments, ultraviolet light source 112 may be recessed within or otherwise engaged with face portion 106 such that the ultraviolet light is multi-directionally emitted (i.e., toward the cover member 114 which may include a reflective interior surface) to interact with face portion 106, as shown in FIG. 3C.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A sterilization device for a stethoscope having a chestpiece member, the chestpiece member having a face portion adapted to contact a patient, the sterilization device comprising:
    a cover member adapted to operably engage the chestpiece member such that the cover member is movable with respect to the face portion between a closed position covering the face portion and an open position uncovering the face portion, while remaining operably engaged with the chestpiece member, and the cover member being normally biased to cover the face portion; and
    an ultraviolet light source operably engaged with the cover member and configured to emit ultraviolet radiation for interacting with the face portion only when the cover member is covering the face portion, the ultraviolet light source thereby providing anti-microbial sterilization of at least the face portion of the chestpiece member.

2. A sterilization device according to claim 1, wherein the cover member is pivotably attached to the chestpiece member such that the cover member rotates substantially parallel to the face portion so as to swivel laterally with respect thereto for selectively covering and uncovering the face portion.

3. A sterilization device according to claim 1, wherein the cover member is pivotably attached to the chestpiece member such that the cover member rotates substantially perpendicularly to the face portion in a flip-over configuration with respect thereto for selectively covering and uncovering the face portion.

4. A sterilization device according to claim 1, further comprising a biasing member operably engaged between the cover member and the chestpiece member, the biasing member being configured to normally bias the cover member to cover the face portion.

5. A sterilization device according to claim 1, wherein the cover member is further configured to form a seal with the face portion, when covering the face portion, so as to cooperate therewith to contain the ultraviolet radiation emitted by the ultraviolet light source.

6. A sterilization device according to claim 1, wherein the cover member further comprises an interior surface directed toward the face portion when the cover member is covering the face portion, the interior surface being further configured to reflect the ultraviolet radiation toward the face portion.

7. A sterilization device according to claim 1, wherein the ultraviolet light source comprises at least one light emitting diode capable of emitting the ultraviolet radiation.

8. A sterilization device according to claim 1, further comprising an attachment element configured to attach the cover member to the chestpiece member.

9. A sterilization device according to claim 1, further comprising an actuation device operably engaged between the cover member and the chestpiece member, the actuation device being configured to actuate the ultraviolet light source only when the cover member is covering the face portion.

10. A stethoscope comprising:
a chestpiece member having a face portion adapted to contact a patient and to transmit sound therefrom to a binaural member; and
an ultraviolet light source operably engaged with and incorporated into the chestpiece member, the ultraviolet light source being configured to emit ultraviolet radiation for interacting with the face portion to provide antimicrobial sterilization of at least the face portion of the chestpiece member.

11. A stethoscope according to claim 10, further comprising a cover member configured to operably engage the chestpiece member such that the cover member is movable with respect to the face portion and normally biased to cover the face portion.

12. A stethoscope according to claim 11, wherein the ultraviolet light source is further configured to emit the ultraviolet radiation for interacting with the face portion only when the cover member is covering the face portion.

13. A stethoscope according to claim 11, wherein the cover member is pivotably attached to the chestpiece member such that the cover member rotates substantially parallel to the face portion so as to swivel laterally with respect thereto for selectively covering and uncovering the face portion.

14. A stethoscope according to claim 11, wherein the cover member is pivotably attached to the chestpiece member such that the cover member rotates substantially perpendicularly to the face portion in a flip-over configuration with respect thereto for selectively covering and uncovering the face portion.

15. A stethoscope according to claim 11, further comprising a biasing member operably engaged between the cover member and the chestpiece member, the biasing member being configured to normally bias the cover member to cover the face portion.

16. A stethoscope according to claim 11, wherein the cover member is further configured to form a seal with the face portion, when covering the face portion, so as to cooperate therewith to contain the ultraviolet radiation emitted by the ultraviolet light source.

17. A stethoscope according to claim 11, wherein the cover member further comprises an interior surface directed toward the face portion when the cover member is covering the face portion, the interior surface being further configured to reflect the ultraviolet radiation toward the face portion.

18. A stethoscope according to claim 11, wherein the ultraviolet light source is operably engaged with the cover member and configured to emit the ultraviolet radiation toward the face portion.

19. A stethoscope according to claim 11, wherein the ultraviolet light source is further configured to be operably engaged with the face portion so as to emit the ultraviolet radiation toward the cover member.

20. A stethoscope according to claim 11, further comprising an attachment element configured to attach the cover member to the chestpiece member.

21. A stethoscope according to claim 11, further comprising an actuation device operably engaged between the cover member and the chestpiece member, the actuation device being configured to actuate the ultraviolet light source only when the cover member is covering the face portion.

22. A stethoscope according to claim 10, wherein the ultraviolet light source comprises at least one light emitting diode capable of emitting the ultraviolet radiation.

23. A stethoscope according to claim 10, wherein the face portion of the chestpiece member comprises an ultraviolet radiation-transparent material, and the ultraviolet light source is disposed within the chestpiece member such that ultraviolet radiation emitted therefrom is directed through the ultraviolet radiation-transparent material to provide anti-microbial sterilization of at least the face portion of the chestpiece member.

* * * * *